(12) United States Patent
Chinn

(10) Patent No.: US 6,596,024 B2
(45) Date of Patent: Jul. 22, 2003

(54) POLYMERIC HEART VALVE FABRICATED FROM POLYURETHANE/POLYSILICONEURETHANE BLENDS

(75) Inventor: Joseph Andrew Chinn, Austin, TX (US)

(73) Assignee: Carbomedics Inc., Austin, TX (US)

( * ) Notice: Subject to any disclaimer, the term of this patent is extended or adjusted under 35 U.S.C. 154(b) by 0 days.

(21) Appl. No.: 09/746,280

(22) Filed: Dec. 21, 2000

(65) Prior Publication Data
US 2002/0082689 A1 Jun. 27, 2002

(51) Int. Cl.⁷ .................................................. A61F 2/24
(52) U.S. Cl. ..................... 623/2.17; 623/2.42; 623/926; 525/458; 523/112
(58) Field of Search .............................. 623/2.17, 2.19, 623/2.42, 926; 525/458; 523/112

(56) References Cited

U.S. PATENT DOCUMENTS

| | | | | |
|---|---|---|---|---|
| 4,265,694 A | * | 5/1981 | Boretos et al. | 156/242 |
| 4,786,556 A | * | 11/1988 | Hu et al. | 428/412 |
| 4,939,007 A | * | 7/1990 | Hu et al. | 428/34.1 |
| 5,032,666 A | * | 7/1991 | Hu et al. | 528/70 |
| 5,084,315 A | * | 1/1992 | Karimi et al. | 428/36.6 |
| 6,171,335 B1 | * | 1/2001 | Wheatley et al. | 623/2.17 |

OTHER PUBLICATIONS

Ward, R.S., "ThermoplasticSilicone–UrethaneCopolymers: A New Class of Biomedical Elastomers",Medical Device & Diagnostic Industry, Apr. 2000.
Akutsu, T., et al., "Polyurethaneartificial heart valves in animals",J. Appl. Physiol. 1959, 14, 1045–1048.
Bernacca, G.M., et al., "Hydrodynamicfunction of polyurethaneprosthetic heart valves: Influences of Young's modulus and leaflet thickness,"Sixth World Biomaterials Congress Transactions,Society for Biomaterials, Minneapolis,MN, 2000, p. 584.
Bernacca, G.M., et al., "Polyurethane heart valve durability: effects of leaflet thickness and material," The International Journal of Artificial Organs,1997, 20:327–331.
Coleman,D.L., "Mineralizationof Blood Pump Bladders", Trans. Am. Soc. Artif. Inter. Organs, 1981, 27:708–713.
Fisher,J., et al. "A new design of polymer synthetic leaflet heart valve," Sixth World BiomaterialsCongress Transactions,Society for Biomaterials,Minneapolis,MN, 2000, p. 68.
Hanson,S.R., et al., "In vivo evaluation of artificial surfaces with a nonhuman primate model of arterial thrombosis," J. Lab. Clin. Med., 1980, 95:289–304.
Hilbert, S.L. et al., "Evaluation of explanted polyurethane trileaflet cardiac valve prostheses," J. Thorac Cardiovasc Surg, 1987, 94: 419–29.
Martin, D.K., et al. "Polydimethylsioxane/polyethermixed–macrodiol–based polyurethane elastomers:biostability," Biomaterials,2000, 21:1021–1029.
Shoen, et al., "Biomaterial–assistedcalcification: Pathology, mechanisms, and strategies for prevention," J. Biomed. Mater. Res.: Applied Biomaterials,1988 vol. 22 A1, 11–36.
Thoma,RJ, et al. "Ionic Interactionsof Polyurethanes," Journal of Biomaterials Applications,1988, 3:180–206.
Ward, RS, et al. "High–strength,optically clear, silicone–urethanethermoplasticsfor biomedicaluse: Bulk properties,"Sixth World Biomaterials Congress Transactions,Society for Biomaterials,Minneapolis,MN 2000, p. 431.
Ward, RS, "Surface modification prior to surface formulation: control of polymer surface properties via bulk composition," Medical Plastics and Biochemicals,1995, 2:34–41.

\* cited by examiner

Primary Examiner—Paul B. Prebilic
(74) Attorney, Agent, or Firm—Williams, Morgan & Amerson, P.C.

(57) ABSTRACT

Biocompatible prostheses, specifically, biocompatible heart valves, are described which comprise a blend of a polyurethane (PU) and a polysiliconeurethane (PSU). Preferably, the polyurethane is a polyetherurethane (PEU). More preferably, it is a polyetherurethane urea (PEUU). Such prostheses typically exhibit reduced mineralization or thrombosis and/or reduced biological degradation.

12 Claims, 1 Drawing Sheet

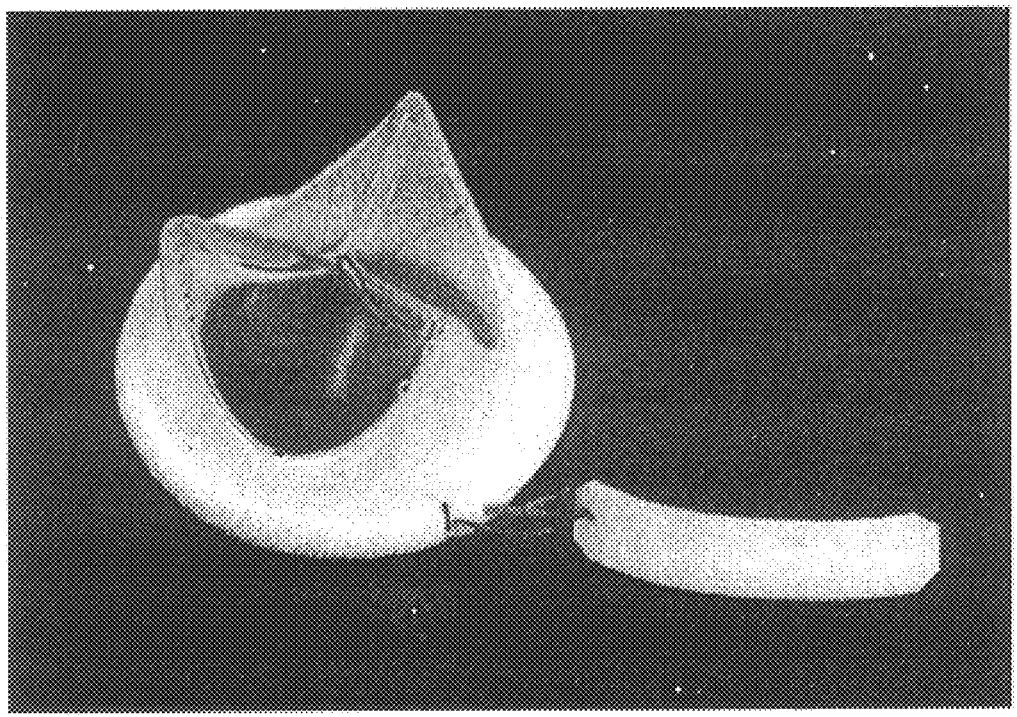
Figure 1. Photograph of a Penn State design polymer heart valve, fabricated of HP-100 silicone rubber.

POLYMERIC HEART VALVE FABRICATED FROM POLYURETHANE/ POLYSILICONEURETHANE BLENDS

BACKGROUND OF THE INVENTION

The present invention relates generally to the field of biocompatible prosthetic devices having good mechanical properties and good hemocompatibility. More particularly, it concerns biocompatible heart valves fabricated from a blend of a polyurethane (PU) and a polysiliconeurethane (PSU).

DESCRIPTION OF RELATED ART

Continuing advances in prosthetic heart valve design and techniques for their implantation have improved the survival time and quality of life for patients who receive these devices. In an ongoing effort to develop more durable and compatible heart valve prostheses, researchers have used a variety of techniques to determine the suitability of given valve materials for a given implant application. This suitability is generally known as "biocompatibility." Researchers commonly deal with biocompatibility in terms of whether the implant material or its degradation products, if any, initiate adverse tissue responses in the host, or conversely, whether deleterious changes in the chemical, physical, or mechanical properties of the implant material are caused by the host environment. The term "hemocompatibility" refers more specifically to biocompatibility issues related to implantation of prosthetic devices (such as prosthetic heart valves and vascular or coronary stents) in the cardiovascular system, such as any toxicity of implant materials to red blood cells or tissues contacted by the implanted material, thrombosis, and induction of mineralization. The vast majority of biocompatibility studies to date have involved in vitro testing or animal models. However, the ultimate test for biocompatibility of a material, device, or prosthesis is human implantation.

To be clinically effective, a heart valve must endure a difficult environment, including cyclic bending stresses on the leaflets and high pressure transients across the valve, for long periods of time. Prosthetic heart valves currently in clinical use are of two general varieties: mechanical or tissue. Mechanical heart valves are very durable, but their use is complicated by higher risks of thromboembolism, hemorrhage, and hemolysis. Use of mechanical heart valves suffers the further complication of requiring chronic systemic anticoagulation of the patient. Tissue valves require no chronic anticoagulation, on the other hand, but often fail in a far shorter period of time than mechanical valves due to mineralization (the formation of mineral deposits, e.g. calcium phosphates) and tissue tearing.

Potential alternative materials that are sufficiently durable and blood compatible for use in a prosthetic heart valve include (i) non-glutaraldehyde fixed bovine pericardial tissue, which studies in an ovine mitral model have shown to be mineralized to a lesser extent than glutaraldehyde-fixed tissue and (ii) synthetic polymers, such as polyurethanes, which have been reported in many different models to also show less mineralization than glutaraldehyde-fixed bovine pericardial tissue.

Mineralization, however, remains an obstacle to the clinical development of a polymer-based heart valve. Artificial heart valve bladders and pacemaker leads fabricated of polyurethane have been observed to undergo mineralization in mammalian trials. The precise mechanism for pathological mineralization of cardiovascular tissue or heart valve prostheses is not well understood. Generally, the term "pathologic mineralization" refers to deposition of minerals, typically calcium phosphate mineral salts, in association with a disease process. See Schoen et al., "Biomaterial-assisted calcification: Pathology, mechanisms, and strategies for prevention," *J. Biomed. Mater. Res.: Applied Biomaterials*, Vol. 22 A1, 11–36 (1988), incorporated herein by reference.

Mineralization may be due to host factors, implant factors, or extraneous factors such as mechanical stress, or combinations of the foregoing. Some evidence suggests calcium deposits are related to devitalized cells, especially membrane cells, where the calcium pump ($Ca^{+2}$-$Mg^{+2}$-ATPase) responsible for maintaining low intracellular calcium levels is weakened or no longer functioning. Mineralization has been observed to begin with an accumulation of calcium and phosphorous (present as hydroxyapatite and other calcium phosphates), which develops into nodules that can eventually lead to a valve failure.

A permanent implantable prosthetic polymeric heart valve was first described at least four decades ago (Akutsu, T., Dreyer, B., Kolff, W. J., *J. Appl. Physiol.* 14:1045–1048 (1959)), yet reduction of the concept to clinical practice has eluded the medical device industry, due to leaflet stiffening, tearing, thrombosis, calcification, and valve stenosis not predicted by in vitro models. Reported physical properties of materials such as polyetherurethanes exceed the requirements of cardiac valves. Biomer, a polyetherurethane urea once thought to be the ideal blood contacting material for implantable devices such as heart valves, was later reported to be prone to mineralization in the juvenile sheep model (Hilbert, S. L. et al., *J. Thorac. Cardiovasc. Surg.* 94: 419–429 (1987)), and its use as a primary component of a clinical prosthetic heart valve has not materialized. While the observed mineralization was first attributed to microscopic defects in the leaflet surface, it was later appreciated that the polyether segment of the polyurethane has the capacity to associate with calcium ions in the blood, thereby leading to mineralization of the material itself (Thoma, R. J. et al., *J. Biomat. Appl.* 3:180–206 (1988)). Reports of mineralized polyurethane blood pump bladders supported the polyurethane mineralization theory (Coleman, D. L. *Trans. Am. Soc. Artif. Intern. Organs* 27: 708–713 (1981)). However, it was not appreciated that mineralized thrombus comprised the vast majority of the calcium present upon polymer valve leaflets, and therefore, for materials not inherently calcific, inhibition of leaflet thrombosis simultaneously prevents leaflet calcification.

The location of mineralization sites on a heart valve prosthesis may be intrinsic, i.e., within the boundaries of the biomaterials of the prosthesis, or extrinsic, i.e., outside the biomaterials, though possibly attached to the valve prosthesis, e.g., within thrombus or other adherent tissue. With polymer valves, it is generally believed that both intrinsic and extrinsic mineralization must be controlled. Therefore, a biocompatible heart valve prosthesis is needed that is resistant not only to thrombus formation, but also to mineralization, particularly extrinsic mineralization, i.e., mineralization of thrombus or tissue adherent to valve leaflets. At the same time, the heart valve prosthesis should possess good mechanical properties to allow it to function adequately for a relatively long time. Despite the demonstrated need, a polymer suitable for long-term implantation as a primary component of a heart valve has remained elusive.

Polyetherurethane (PEU) is typically synthesized from a diisocyanate (such as diphenylmethane-4,4'-diisocyanate (MDI)), a diol chain extender (such as 1,4-butanediol (BD)), and a polytetramethylene oxide with a molecular weight of about 2000 (PTMO-2000) (available under the trade name Terethane 2000 Polyether Glycol, Dupont, Wilmington, Del.) or other polyalkylene oxide as soft segment. Polyetherurethane urea (PEUU) is typically synthesized using MDI, PTMO, and ethylene diamine (ED) or other diamine chain extender. Both PEU and PEUU have the mechanical properties required to provide prosthesis durability in accelerated fatigue testing as described by Bemacca G M et al., "Polyurethane heart valve durability: effects of leaflet thickness and material," *Int. J. Artif Organs,* 20, 327–331 (1997), incorporated herein by reference. However, other chain extenders, e.g., alkyl diols or diamines and other soft segments, e.g., polycarbonate having two isocyanate-reactive terminal groups such as poly(1,6-hexyl 1,2-ethyl carbonate) diol or polyalkylene oxide, such as polyhexamethylene oxide (PHMO), can also be used.

Polysiliconeurethane (PSU) (a.k.a., silicone-urethane copolymer) is typically synthesized using MDI, BD, and a polydiorganosiloxane having two isocyanate-reactive terminal groups, such as polydimethylsiloxane (PDMS) end capped with alkyl alcohol as soft segment. The high surface activity of PDMS results in its relatively higher surface concentration relative to its bulk concentration. Due to the better hemocompatibility of silicone rubber relative to polyetherurethane as described in Hanson S R et al., "In vivo evaluation of artificial surfaces with a nonhuman primate model of arterial thrombosis," *J. Lab. Clin. Med.,* 95, 289–304 (1980), incorporated herein by reference, PSU also provides better hemocompatibility than either PEU or PEUU. However, PSU has thus far lacked the mechanical strength, fatigue resistance, and durability of either PEU or PEUU needed for a durable prosthetic heart valve.

Hybrid polymers containing both polyether and polydiorganosiloxane soft segments can also be made. Martin D K et al., "Polydimethylsiloxane/polyether-mixed macrodiol-based polyurethane elastomers: biostability," *Biomaterials,* 21, 1021–1029 (2000), incorporated herein by reference, describe polyurethanes synthesized using MDI and BD as hard segment, and mixtures of polyhexamethylene oxide (PHMO) and polydimethylsiloxane (PDMS) macrodiols as soft segment. While the mechanical strength of the polymer increases with the fraction of PHMO used in the synthesis, the biodegradation resistance increases with the fraction of PDMS. The authors report that a PHMO:PDMS ratio of 1:4 provides the optimum polymer in terms of flexibility, strength, and biostability.

G M Bemacca et al., "Hydrodynamic function of polyurethane prosthetic heart valves: Influences of Young's modulus and leaflet thickness," in *Sixth World Biomaterials Congress Transactions,* Society for Biomaterials, Minneapolis, Minn., 2000, p. 584, and Fisher and M Butterfield, "A new design of polymer synthetic leaflet heart valve," in *Sixth World Biomaterials Congress Transactions,* Society for Biomaterials, Minneapolis, Minn., 2000, p. 68, report in vitro studies of tri-leaflet heart valves, wherein the leaflets of the different valves comprised different polysiliconeurethanes (commercially available under the trade name Elast-Eon™, Elastomedic Pty Ltd., Chatswood, Australia).

Ward R S, "Surface Modification Prior to Surface Formulation: Control of Polymer Surface Properties Via Bulk Composition," Medical Plastics and Biochemicals, 2, 34–41, 1995, describes XPS analysis of PEU modified with less than 5% w/w PDMS ends groups that finds the surface to be essentially PDMS. Furthermore, Ward R S et al., "High-strength, optically clear, silicone-urethane thermoplastics for biomedical use: Bulk properties," in *Sixth World Biomaterials Congress Transactions,* Society for Biomaterials, Minneapolis, Minn., 2000, p. 431, describes PSU/PEU hybrid copolymers varying in ratio of polyether to polysilicone in the soft segment (from all polysilicone to >99%, w/w, polyether).

Without being bound by any particular theory, it is believed that the high surface activity of PDMS and similar silicone-based polymer segments can be exploited to achieve a polymeric heart valve with a surface concentration of PDMS far exceeding the bulk concentration of PDMS in a copolymer or a polymer mixture.

SUMMARY OF THE INVENTION

This invention relates to biocompatible heart valve prostheses comprising a blend of a polyurethane and a polysiliconeurethane. More particularly, this invention relates to biocompatible prostheses that are hemocompatible and resistant to in vivo mineralization and/or biological degradation.

In one embodiment, the invention is directed to a prosthetic heart valve comprising a stent defining a blood flow path and a plurality of leaflets, each leaflet comprising a blend of a polyurethane and a polysiliconeurethane.

In another embodiment, the invention relates to a method of reducing mineralization or thrombosis of an implanted prosthesis, comprising (i) prior to implantation, fabricating the prosthesis from a blend of a polyurethane and a polysiliconeurethane, and (ii) implanting the prosthesis.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 is a photograph of a Penn State design polymer heart valve, fabricated of silicone rubber (HP-100).

DESCRIPTION OF ILLUSTRATIVE EMBODIMENTS

In one embodiment, the present invention provides a biocompatible prosthesis comprising a blend of a polyurethane and a polysiliconeurethane. Such a biocompatible prosthesis typically has improved resistance to mineralization and improved resistance to thrombus formation. Such a prosthesis also typically is less susceptible to biological degradation than is a prosthesis consisting essentially of a polyurethane. Any prosthesis for which biocompatibility is desired can be fabricated from the blend. In a preferred embodiment, the prosthesis is a heart valve.

Though not to be bound by any particular theory, it is believed that mineralization of vascular prostheses most commonly occurs at sites where thrombus has adhered to the prosthesis. In particular, observations of polymer heart valves have shown that most mineralization occurs at sites of thrombus formation. Therefore, it is believed that the vascular prostheses of the present invention reduce mineralization by reducing thrombus formation.

The polyurethane (PU) component of the polymer blend can be any polyurethane having mechanical properties appropriate for a polymer prosthesis. In one embodiment, the polyurethane is a polyetherurethane (PEU), a polyetherurethane urea (PEUU), or a polycarbonateurethane (PCU). An exemplary preferred polyurethane is a polyetherurethane urea (PEUU) available under the trade name BioSpan™ (The Polymer Technology Group, Berkeley, Calif.). Another exemplary preferred polyurethane is a polycarbonateurethane (PCU) available under the trade name Bionate™ (The Polymer Technology Group). The polyurethane component may be commercially obtained from a variety of suppliers, or it may be readily synthesized by those skilled in the art. If the polyurethane is a PEU or a PEUU, it may comprise a soft segment component, such as polytetramethylene oxide (PTMO) or polyhexamethylene oxide (PHMO), among others.

The polysiliconeurethane (PSU) component of the blend can be any polymer that contains a polysiliconeurethane in at least part of the soft segment. Exemplary PSU's include polysiliconeurethane and mixed macrodiol-based polyurethanes (such as PSU/PEU copolymer or PSU/PCU copolymer), among others. The PSU may be commercially obtained from a variety of suppliers, or it may be readily synthesized as part of the process of prosthesis fabrication. For example, PSU is available from Dow Coming, Midland, Mich., as X7-4074. The Polymer Technology Group Inc., Berkeley, Calif., also manufactures PSU, as well as PurSil™, a family of silicone-polyetherurethane copolymers, and CarboSil™, a family of silicone-polycarbonateurethane copolymers.

The concentrations of the polyurethane (PU) and the polysiliconeurethane (PSU) in the blend can be any concentrations, provided the polyurethane (PU) is present at sufficiently high concentration to provide useful mechanical properties to the prosthesis comprising the blend and the polysiliconeurethane (PSU) is present at sufficiently high concentration to provide biocompatibility to the prosthesis comprising the blend. In a preferred embodiment, the weight ratio of the polyurethane to the polysiliconeurethane in the blend is from about 1:99 to about 9:1. More preferably, the weight ratio is from about 1:5 to about 1:1.

Preferably, the bioprosthesis is a heart valve. A heart valve can also comprise materials other than the polyurethane/polysiliconeurethane (PU/PSU) blend. For example, the valve can be either a stented valve or a stentless valve, although stented valves are preferred. For stented valves, the stent material is typically a hard polymer, such as high durometer polyurethane, polyacetal, or another polymer with a nigh degree of stiffness. However, other stent materials, for example, metals such as titanium alloy or Nitinol®, can be used.

A heart valve according to the present invention preferably comprises two or more leaflets, typically three. Preferably, the leaflets comprise the polyurethane/polysiliconeurethane (PU/PSU) blend.

Heart valves comprising the polyether/polysiliconeurethane (PU/PSU) blend may be constructed as follows. The polyurethane (PU) is dissolved in a first solvent, e.g. an amide such as dimethylacetamide (DMAC) or dimethylformamide (DMF), and the polysiliconeurethane is dissolved in a second solvent, e.g. tetrahydrofuran (THF). Other solvents may be employed without departing from the scope of the invention; however, it is desirable that the first solvent and the second solvent be miscible. Selection of suitable solvents for particular polymers is within the level of ordinary skill in the art.

Typically, the polyurethane (PU) and the polysiliconeurethane (PSU) are each dissolved to about 8–14% w/v, more preferably about 10% w/v, although this concentration can be varied as desired without departing from the spirit and scope of the invention. After the polyurethane (PU) and the polysiliconeurethane (PSU) are dissolved, the polymer solutions are combined into a polymer blend solution. A stent is repeatedly dipped into the polymer blend solution and dried in air at about 15–25% relative humidity, preferably about 20% relative humidity, to form a blend-coated stent. The blend-coated stent is then placed over a leaflet mandrel, which is dipped several times into the solution and dried as above, to provide a heart valve with leaflets of a desired thickness.

Other techniques for the formation of a heart valve comprising the blend may be used. In addition to the dipping technique described herein, the valve may be formed by injection, transfer, or compression molding, thermoforming, or other techniques known in the art, depending on the suitability of the particular polymers selected for the technique. For example, PEUU is not generally suitable for injection molding.

However constructed, the heart valves of the present invention comprise a blend of a polyurethane (PU) and a polysiliconeurethane (PSU). The polyurethane (PU) component of the blend imparts good mechanical properties to the heart valve, and the polysiliconeurethane (PSU) component of the blend imparts resistance to in vivo mineralization or in vivo thrombus formation, and/or biological degradation, to the heart valve.

In another embodiment, the invention relates to a method of reducing mineralization or thrombosis in an implanted prosthesis, comprising (i) prior to implantation, fabricating at least a portion of the prosthesis from a blend of a polyurethane (PU) and a polysiliconeurethane (PSI), and (ii) implanting the prosthesis.

The prosthesis can be fabricated as described above, or according to other techniques apparent to one of ordinary skill in the art. Preferably, substantially all of the surface of the prosthesis comprises the blend.

Implanting the prosthesis can be performed following any technique known in the art to be appropriate for the implantation of the prosthesis, which will vary depending on the nature of the prosthesis and other factors apparent to one of ordinary skill in the art. The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Preparation of Cast-Blended Polyetherurethane Urea-Polysiliconeurethane Valves

Heart valves comprising blended polyetherurethane urea-polysiliconeurethane (PEUU/PSU) according to the present invention are prepared by dip casting. The additional materials used in fabrication are high purity nitrogen gas, compressed oxygen gas, silicone rubber, Ivory soap (Proctor and Gamble, Cincinnati, Ohio), isopropanol, Isoplast 202 (Dow Chemical, Midland, Mich.), tetrahydrofuran (THF), and dimethylacetamide (DMAC). Testing of the heart valves may be facilitated by fabricating the valves in a known design such as the Penn State heart valve (FIG. 1).

A. Solution Preparation: A 10% solution of polysiliconeurethane (PSU) (X7-4074, Dow Coming) in THF is prepared, as is a 10% (w/w) solution of BioSpan PEUU (The Polymer Technology Group Inc., Berkeley, Calif.) in 50% (v/v) THF/DMAC. A blended polymer solution is prepared by mixing equal volumes of the two solutions and shaking for 24 hr. Alternatively, 10% (w/w) solutions of PSU/PEU and PEUU (PurSil™-40 and BioSpan, both from Polymer Technology Group Inc., Berkeley, Calif.) are prepared in THF and DMAC, respectively, and blended to obtain a PSU/PEU/PEUU solution suitable for another embodiment of the present invention.

B. Stent Preparation: A hard polymer stent machined from Isoplast 202 rod stock is washed in isopropanol using an ultrasonic water bath. Using forceps, the stent is placed in an oxygen plasma chamber and plasma etched for 1 hr. The stent is then removed from the plasma chamber and immediately submerged in the 10% PSU/THF (or 10% PSU/PEU in THF) solution for 10 min. This dip is intended to minimize contamination of the stent material. The stent is then removed and excess solution allowed to run off.

C. Stent Dip Casting: The prepared stent is placed in a 3-prong plastic valve stent holder, the holder attaching along the annulus of the stent so that stent tips are dipped first. The stent is then dipped into the blended PSU/PEUU solution (or alternatively the blended PSU/PEU/PEUU solution) to the base of the stent tips a sufficient number of times so that the stent fits snugly over a leaflet mandrel of a predetermined diameter. After each dip, the stent is allowed to rotate dry under nitrogen. Typically, the stent is dipped seven times, although this varies based upon stent width and solution concentration changes due to evaporation.

D. Valve Dip Casting: All aluminum surfaces of a leaflet mandrel are first cleaned using water or isopropanol and a non-abrasive cloth or towel. The leaflet mandrel is dip coated by hand in 3% (w/v) Ivory soap solution (releasing agent) and allowed to rotate under dry nitrogen for at least 30 min. The dip cast PSU/PEUU (or PSU/PEU/PEUU) coated stent is then placed over the leaflet mandrel and repeatedly dipped into the blended PSU/PEUU (or blended PSU/PEU/PEUU) solution to produce leaflets of a desired thickness, typically 6–7 dips. Between each dip, the mandrel is rotated dry under dry nitrogen. After the last dip, both the stent and the mandrel are allowed to dry for 1 hr. The valve is dried overnight in a vacuum oven at 50° C., after which water is applied to remove excess releasing agent.

Example 2

Preparation of Injection Molded Blended Polyetherurethane-Polysiliconeurethane Valves Heart valves comprising blended polyetherurethane-polysiliconeurethane (PEU/PSU) according to the present invention are prepared by injection molding.

A. Blend Preparation: A 10% (w/w) solution of polysiliconeurethane (PSU) (X7-4074, Dow Corning) in THF is prepared, as is a 10% (w/w) solution of Pellethane PEU (Dow Chemical, Midland, Mich.) in DMF. A blended polymer solution is prepared by mixing equal volumes of the two solutions and shaking for 24 hr. The solvent is evaporated and the polymer dried overnight in a vacuum oven at 50° C.

B. Valve Injection Molding: The PSU/PEU blend described above is injected into a polymer valve mold using the following parameters: clamp pressure=400 psi; injection pressure=250 psi; injection speed=low; shot size=9.0 gm; mold cure time=240 sec; mold temperature=285° F.; cavity fill time=2.5 sec. All of the compositions, methods, and apparatus disclosed and claimed herein can be made and executed without undue experimentation in light of the present disclosure. While the compositions, methods, and apparatus of this invention have been described in terms of preferred embodiments, it will be apparent to those of skill in the art that variations may be applied to the compositions, methods, and apparatus and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A biocompatible heart valve prosthesis, comprising:
   a valve body comprising a blood flow orifice;
   at least one polymeric leaflet coupled to said valve body, said leaflet comprising a homogeneous blend of a polyurethane (PU) and a polysiliconeurethane (PSU).

2. The biocompatible prosthesis of claim 1, wherein the polyurethane is selected from the group consisting of polyetherurethane (PEU), polyetherurethane urea (PEUU), and polycarbonateurethane (PCU).

3. The biocompatible prosthesis of claim 1, wherein the polysiliconeurethane is selected from the group consisting of polysiliconeurethane (PSU), polysiliconeurethane/polyetherurethane (PSU/PEU) copolymer, and polysiliconeurethane/polycarbonateurethane (PSU/PCU) copolymer.

4. The biocompatible prosthesis of claim 1, wherein the weight ratio of PU:PSU in the blend is from about 1:99 to about 9:1.

5. The biocompatible prosthesis of claim 4, wherein the weight ratio of PU:PSU in the blend is from about 1:5 to about 1:1.

6. The biocompatible prosthesis of claim 1, wherein the prosthesis is a heart valve comprising a stent defining a blood flow path, and a plurality of polymeric leaflets comprising a blend of PU and PSU.

7. A method of reducing mineralization, thrombosis, or biological degradation of an implanted prosthesis, comprising:
   mixing a polyurethane (PU) and a polysiliconeurethane (PSU) to form a homogenous polymer blend;
   fabricating at least a portion of the prosthesis from the homogenous polymer blend; and
   implanting the prosthesis.

8. The method of claim 7, wherein the polyurethane is selected from the group consisting of polyetherurethane (PEU), polyetherurethane urea (PEUU), and polycarbonateurethane (PCU).

9. The method of claim 7, wherein the polysiliconeurethane is selected from the group consisting of polysiliconeurethane (PSU), polysiliconeurethane/polyetherurethane (PSU/PEU) copolymer, and polysiliconeurethane/polycarbonateurethane (PSU/PCU) copolymer.

10. The method of claim 7, wherein the weight ratio of PU:PSU in the blend is from about 1:99 to about 9:1.

11. The method of claim 10, wherein the weight ratio of PU:PSU in the blend is from about 1:5 to about 1:1.

12. The method of claim 7, wherein the prosthesis is a heart valve comprising a stent defining a blood flow path, and a plurality of polymeric leaflets comprising a blend of PU and PSU.

* * * * *